United States Patent
Nishikawa et al.

(10) Patent No.: US 7,696,402 B2
(45) Date of Patent: Apr. 13, 2010

(54) ABSORBENT ARTICLE

(75) Inventors: Kumiko Nishikawa, Kagawa-ken (JP); Jun Kudo, Kagawa-ken (JP); Takuya Miyama, Kagawa-ken (JP); Chiemi Habu, Kagawa-ken (JP)

(73) Assignee: Uni-Charm Corporation, Ehime-Ken (JP)

( * ) Notice: Subject to any disclaimer, the term of this patent is extended or adjusted under 35 U.S.C. 154(b) by 176 days.

(21) Appl. No.: 11/427,803

(22) Filed: Jun. 30, 2006

(65) Prior Publication Data

US 2007/0005036 A1    Jan. 4, 2007

(30) Foreign Application Priority Data

Jul. 1, 2005    (JP)    ............... 2005-194361

(51) Int. Cl.
A61F 13/15    (2006.01)
(52) U.S. Cl. ................. 604/380; 604/379; 604/385.101
(58) Field of Classification Search ................. 604/379, 604/380, 385.101
See application file for complete search history.

(56) References Cited

U.S. PATENT DOCUMENTS

| | | | |
|---|---|---|---|
| 7,204,830 B2 * | 4/2007 | Mishima et al. | ........ 604/385.19 |
| 2001/0020157 A1 * | 9/2001 | Mizutani et al. | ....... 604/385.04 |
| 2003/0088222 A1 * | 5/2003 | Yoshimasa et al. | .......... 604/380 |
| 2006/0116653 A1 * | 6/2006 | Munakata et al. | ........... 604/380 |
| 2006/0276767 A1 * | 12/2006 | Ueminami et al. | ..... 604/385.31 |

FOREIGN PATENT DOCUMENTS

JP    2001-8971    6/1999

* cited by examiner

*Primary Examiner*—Tatyana Zalukaeva
*Assistant Examiner*—Lynne Anderson
(74) *Attorney, Agent, or Firm*—Lowe Hauptman Ham & Berner

(57) ABSTRACT

An absorbent article includes a compressed groove provided on a body-side surface of a sanitary napkin includes a pair of lateral groove segments extending substantially in the longitudinal direction symmetrically about a longitudinal center line and a pair of rear groove segments converging rearward from respective rear ends of the pair of lateral groove segments so that the compressed groove as a whole presents an elongated shape which is angular rearward. The rear side groove segment has a curve conforming, in the vicinity of its rear end, with an arc of a circle having a predetermined radius and inscribed to the rear side groove segment. A bottom covering region extending rearward from the rear end of the rear groove segment has a predetermined thickness and is adapted to be folded along the longitudinal center line so that the bottom covering region can become convex on the side of the body-side surface. A distance between a pair of proximal ends of the rear side groove segment as measured in the transverse direction is in a predetermined range and a distance from the pair of proximal ends to the rear end of the rear groove segment as measured in the longitudinal direction is in a predetermined range.

18 Claims, 15 Drawing Sheets

ABSORBENT ARTICLE

BACKGROUND OF THE INVENTION

The present invention relates to an absorbent article and, more particularly, to an absorbent article such as sanitary napkin having an improved fit to the wearer's bottom.

Japanese Unexamined Patent Application Publication No. 2001-8971 (hereinafter referred to as "REFERENCE") discloses an absorbent article which is substantially longer than is wide, comprising an absorbent layer, a leak-barrier layer, a front region formed with one or two leak-barrier groove (s) extending in the longitudinal direction and a rear region formed with three or more leak-barrier grooves. In this article, sealing strength along the leak-barrier grooves is set to 50 cN/30 mm or higher to prevent a possible leak of body fluids due to break and/or peeling off of a topsheet from an absorbent pad.

However, in view of the fact that a zone extending behind the leak-barrier grooves has substantially the same thickness as the remaining zone, any effective and thoughtful consideration for the purpose of improvement in the leak-barrier effect can not be found in this article of prior art. More specifically, even though the zone extending behind the leak-barrier grooves is folded in a transverse direction under a pressure laterally exerted on this zone as the article is put on the wearer's body, it will be difficult for the fold to fit into bottom cleft. Consequently, it will be difficult to prevent body fluids from leaking along the bottom cleft.

SUMMARY OF THE INVENTION

It is an object of the present invention to provide an absorbent article having a sufficient fit into the bottom cleft to assure a high leak-barrier effect.

The object set forth above is achieved, according to the present invention, by an improvement referred to below as first construction or an improvement referred to below as second construction in the absorbent article having a longitudinal direction, a transverse direction, a body-side surface, a clothes-side surface, longitudinally opposed front and rear ends and transversely opposite side edges and comprising a liquid-absorbent layer and a compressed groove on the side of the body-side surface so as to be longer than is wide.

The first construction is in that the compressed groove comprises a pair of lateral groove segments extending substantially in the longitudinal direction symmetrically about a longitudinal center line of the article and a pair of rear groove segments converging rearward from respective rear ends of the pair of lateral groove segments so that the compressed groove as a whole forms an elongated shape which is angular rearward, the rear side groove segment has a curve conforming, in the vicinity of its rear end, with an arc of a circle having a radius in a range of 0 to 10 mm inscribed to the rear side groove segment, and a bottom covering region extending rearward from the rear end of the rear groove segment has a thickness in a range of 1 to 5 mm and is adapted to be folded along the longitudinal center line so that the bottom covering region can become convex on the side of body-side surface.

It should be understood that the radius of 0 mm refers to a case in which the paired rear groove segments are not curved, for example, in circular arcs, but linear, in the vicinity of the rear end.

The second construction is in that the compressed groove comprises a pair of lateral groove segments extending substantially in the longitudinal direction symmetrically about a longitudinal center line of the article and a pair of rear groove segments converging rearward from respective rear ends of the pair of lateral groove segments so that the compressed groove as a whole forms an elongated shape which is angular rearward, a distance between a pair of proximal ends of the rear side groove segment as measured in the transverse direction is in a range of 25 to 55 mm, a distance from the pair of proximal ends to the rear end of the rear groove segment as measured in the longitudinal direction is in a range of 30 to 150 mm, and a bottom covering region extending rearward from the rear end of the rear groove segment has a thickness in a range of 1 to 5 mm and is adapted to be folded along the longitudinal center line so that the bottom covering region can become convex on the side of body-side surface.

During use of the absorbent article provided with the rear side groove segments configured as has been described above and the bottom covering region having the thickness as has been indicated, the lateral pressure due to movement of the wearer's thighs is transmitted to the rear side groove segments and simultaneously the contractile force of the elastic yarns laid on the wearer's shorts causes the bottom covering region to be lifted up from the clothes-side surface toward the body-side surface. Consequently, the rear side groove segments guide the bottom covering region to be smoothly folded along the longitudinal center line and the bottom covering region reliably fits in such folded state into the wearer's bottom cleft.

To ensure that the bottom covering region is smoothly folded along the longitudinal center line and becomes convex on the side of the body-side surface, the bottom covering region has the transverse flexural stiffness preferably in a range of 100 to 400 mg, more preferably 130 to 350 mg. While the flexural stiffness of the region other than the bottom covering region is not specified, the transverse flexural stiffness at the rear end of the rear side groove segments may be set preferably to a range of 100 to 500 mg, more preferably to a range of 150 to 350 mg in order that the bottom covering region can be more smoothly folded.

A zone extending between the pair of lateral groove segments in front of the bottom covering region may be configured to be thicker than the bottom covering region and to protuberate on the side of the body-side surface to improve fitness of the bottom covering region to the wearer's bottom cleft and thereby to achieve further improvement of preventive effect against leak of body fluids.

The respective rear ends of the paired rear side groove segments may be contiguous to each other or not. With these rear ends being contiguous to each other, the paired rear side groove segments preferably converge on the longitudinal center line, in other words, the respective rear ends of these paired rear side groove segments preferably lie on the longitudinal center line. With these rear ends being not contiguous to each other, a middle point on an imaginary line segment extending between these rear ends of the rear side groove segments preferably lies on the longitudinal center line. So far as the rear ends of the paired rear side groove segments are positioned as has been defined above, it is ensured that a fold line appearing during use of the napkin under the guiding effect of the rear side groove segments reliably falls upon the longitudinal center line. Consequently, the bottom covering region can cover the wearer's bottom in laterally balanced manner. It is possible to provide a fold guide extending rearward from the rear end of the compressed groove along the longitudinal center line so that the article can be reliably folded along the longitudinal center line in the bottom covering region.

The compressed groove may further comprise a front side groove segment extending forward from the front ends of the respective lateral groove segments so as to connect these front ends to each other. The compressed groove comprising the lateral groove segments, the rear side groove segment and the front side groove segment may be advantageously formed as a whole in a closed loop. At a glance, the wearer has a sense of reassurance that any amount of body fluids discharged in the region surrounded by the compressed groove never leak. Indeed, the compressed groove formed in the closed loop practically assures leak-barrier effect as high as it looks.

A longitudinal distance from the rear end of the rear side groove segment to the rear end of the liquid-absorbent layer is preferably 50 mm or longer. In this way, the wearer's bottom is covered with the liquid-absorbent layer over an area sufficient to achieve effective prevention of body fluid leak and also to eliminate psychological anxiety on leak.

With the absorbent article according to this invention put on the wearer's body, the bottom covering region is folded along the rear side groove segment and become convex on the side of the body-side surface as the pressure due to movement of the wearer's thighs is exerted on this region. In such folded state, the bottom covering region fits into the wearer's bottom cleft. In this way, fitness of the article to the wearer's bottom is improved and leak of body fluids occurring along the bottom cleft is reliably prevented.

DETAILED DESCRIPTION OF THE PREFERRED EMBODIMENTS

Details of the absorbent article according to the present invention will be more fully understood from the description of a sanitary napkin as a typical embodiment given hereunder in reference with the accompanying drawings.

Figure 1:
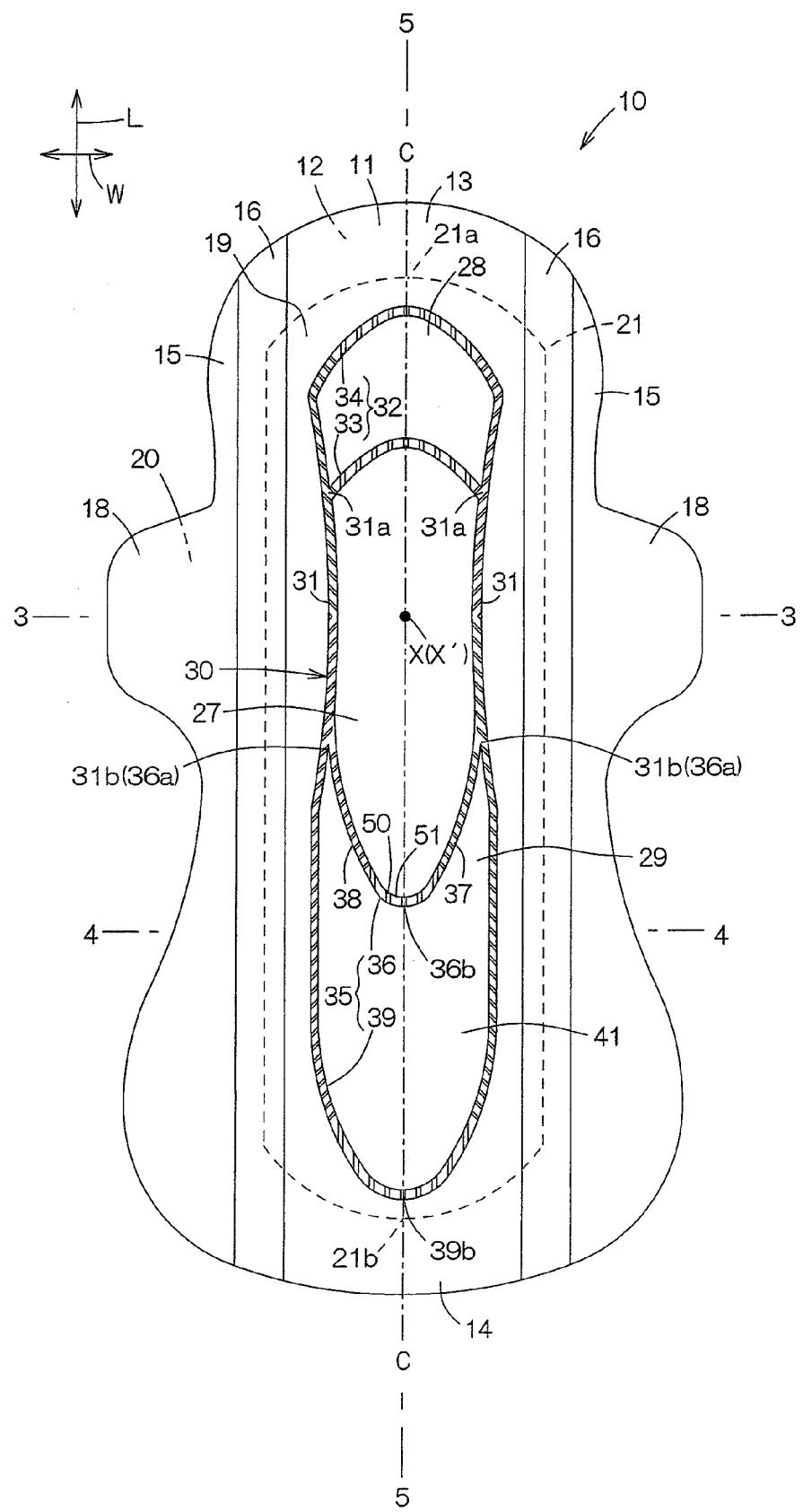
FIG. 1 is a plan view showing sanitary napkin according to this invention.
Figure 2:
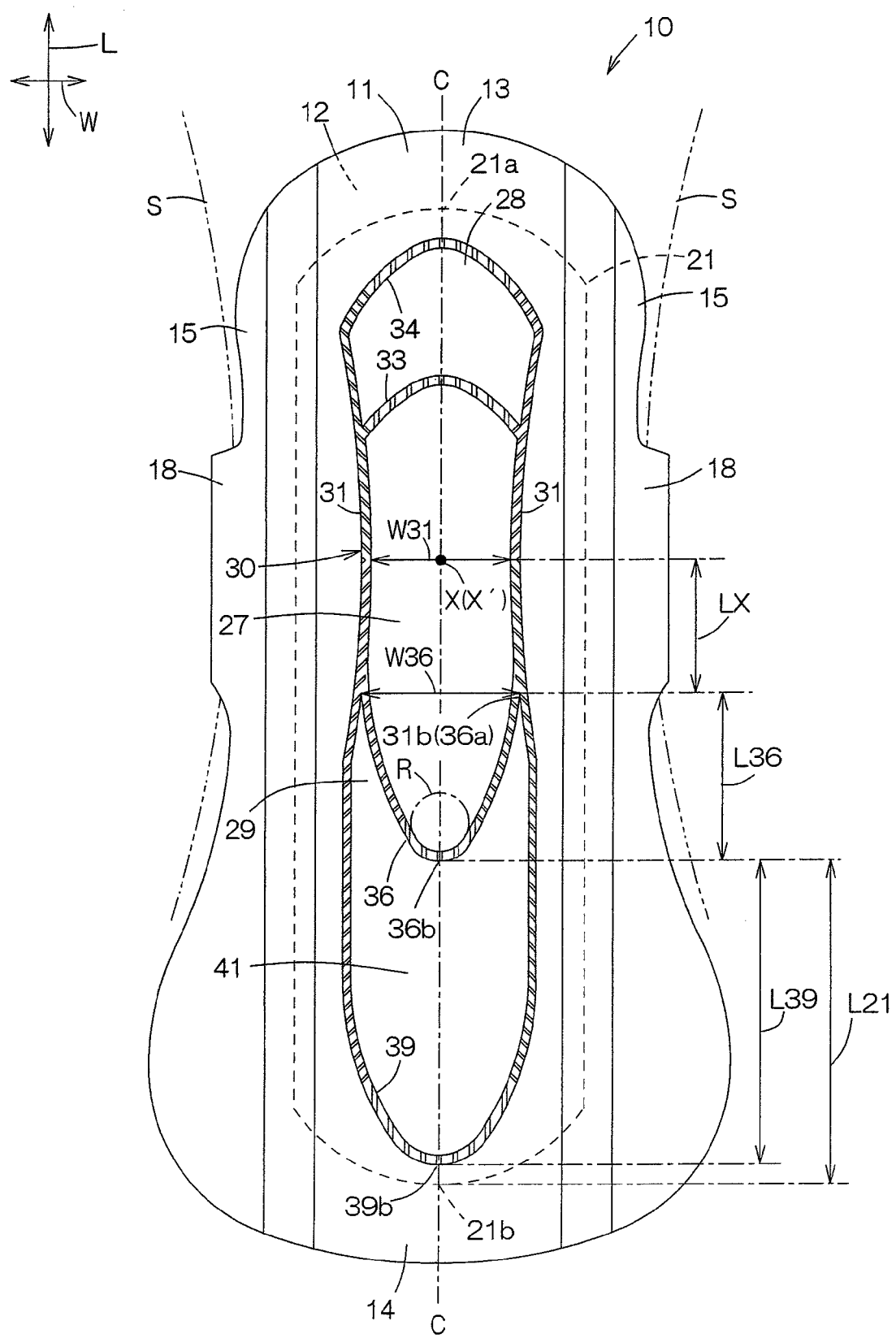
FIG. 2 is a plan view showing the sanitary napkin as fastened to the wearer's shorts.
Figure 3:
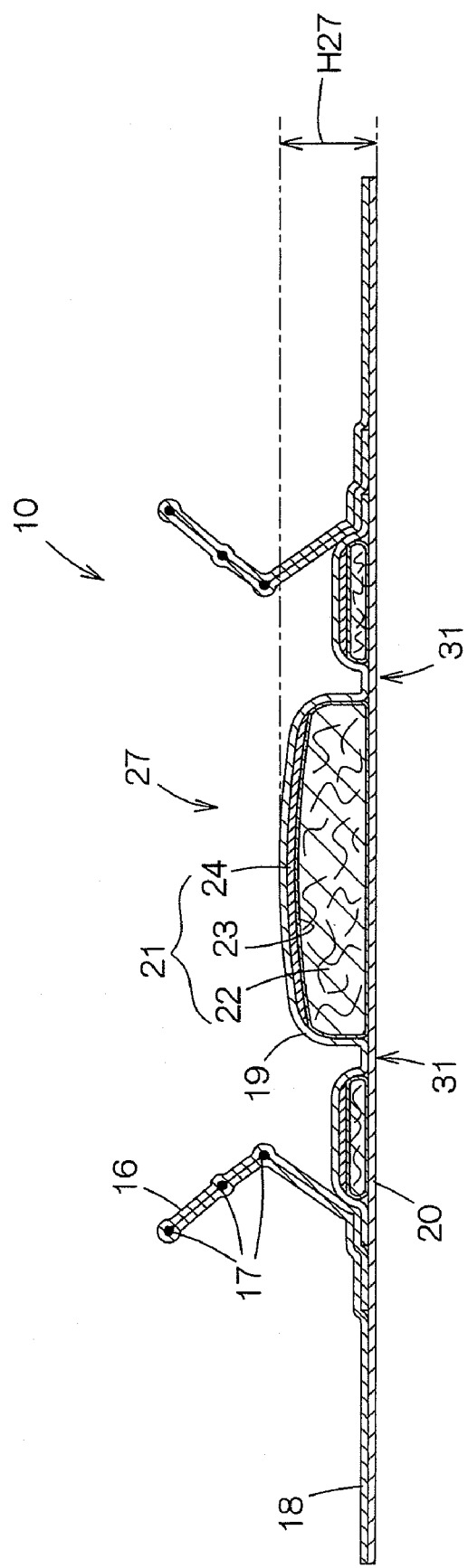
FIG. 3 is a sectional view of the sanitary napkin taken along a line 3-3 in FIG. 1.
Figure 4:
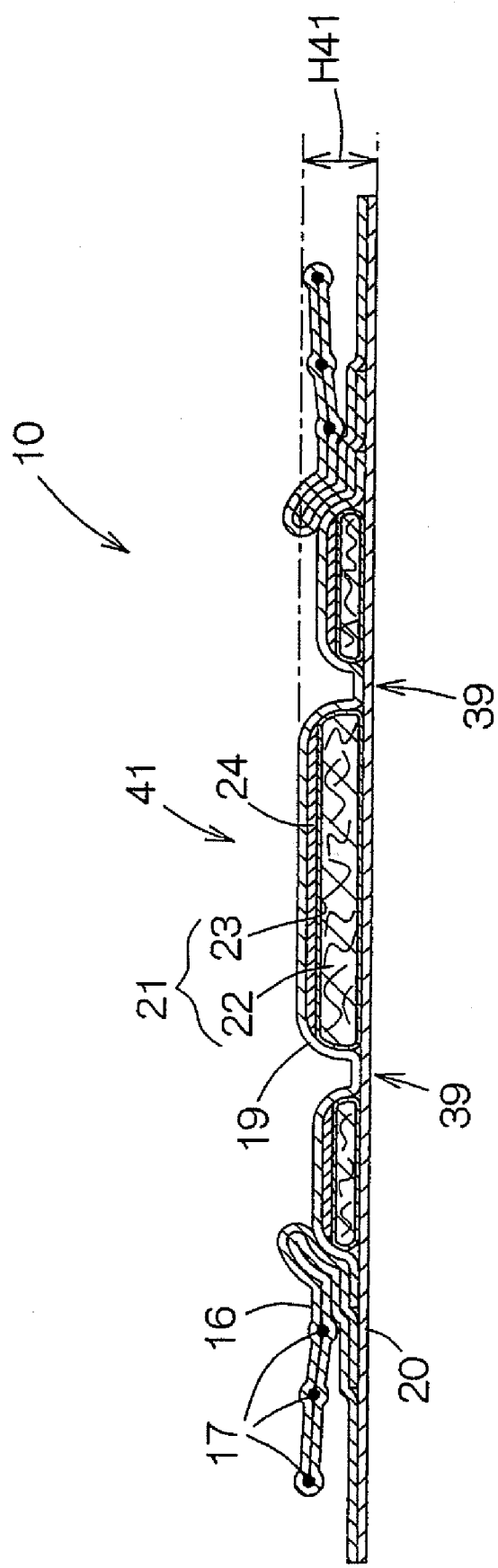
FIG. 4 is a sectional view of the sanitary napkin taken along a line 4-4 in FIG. 1.
Figure 5:
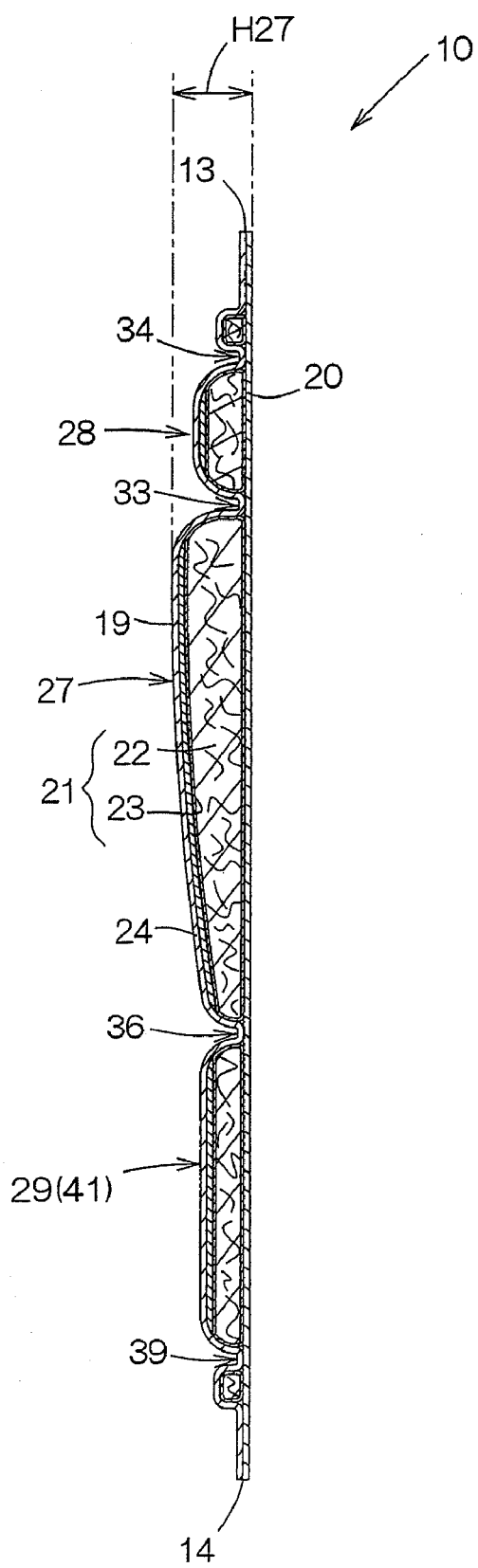
FIG. 5 is a sectional view of the sanitary napkin taken along a line 5-5 in FIG. 1 defined by a longitudinal center line of the sanitary napkin.

FIG. 1 is a plan view showing the sanitary napkin 10 with a body-side surface 11 facing upward. This napkin 10 is substantially in a flat state against a contractile force of elastic members 17 as will be described later. FIG. 2 is a plan view showing the napkin 10 with wings 18 as will be described later having been folded onto the rear surface and fastened to the wearer's shorts S. FIG. 3 is a sectional view of the napkin 10 taken along a line 3-3 in FIG. 1. FIG. 4 is a sectional view of the napkin 10 taken along a line 4-4 in FIG. 1. FIG. 5 is a sectional view of the napkin 10 taken along a line 5-5 in FIG. 1 defined by a longitudinal center line C of the napkin 10.

The napkin 10 is longer than is wide so as to be conveniently put on a menstruating woman while in bed. A full length in the longitudinal direction L is in the order of 200 to 450 mm.

This napkin has the longitudinal direction L, the transverse direction W, the body-side surface 11, a wearer's clothes-side surface 12, front and rear ends 13, 14 opposed to each other in the longitudinal direction L, and side edges 15, 15 opposed to each other in the transverse direction W. The napkin 10 basically comprises a liquid-pervious topsheet 19 defining the body-side surface 11, a liquid-impervious backsheet 20 defining the wearer's clothes-side surface 12 and a liquid-absorbent layer 21 sandwiched between the top- and backsheets 19, 20. The napkin 10 has its outer peripheral edge is sealed together. The liquid-absorbent layer 21 comprises a liquid-absorbent core 22 and a liquid-diffusive sheet 23 wrapping the core 22. The liquid-absorbent layer 21 has a front end 21a and a rear end 21b. A cushion layer 24 adapted to improve fitness as well as a spot absorbency is sandwiched between the topsheet 19 and the liquid-absorbent layer 21.

The napkin 10 includes a pair of leak-barrier flaps 16, 16 extending along the side edges of the liquid-absorbent layer 21 in the longitudinal direction L and a pair of wings 18 provided slightly aside toward the front end 13 so as to extend from the side edges of the napkin 10 in the transverse direction W.

The leak-barrier flaps 16 are fixed at respective front and rear ends as well as at respective outer side edges as viewed in the transverse direction W to the topsheet 19 so that these leak-barrier flaps 16 are laid in the vicinity of the side edges of the liquid-absorbent layer 21. Each of the leak-barrier flaps 16 is provided with a plurality of elastic members 17 (See FIGS. 3 and 4) extending in the longitudinal direction L and contractile force of these elastic members 17 causes the leak-barrier flap 16 to rise and thereby to form a barrier against menstrual blood. The elastic members 17 are attached in stretched state to the leak-barrier flaps 16 in a manner that the elastic contractile force thereof primarily acts on zones in which side grooves 31, as will be described later, are laid.

The wings 18 are defined by extensions of the leak-barrier flaps 16 and the backsheet 20. It is possible to interpose reinforcing members (not shown) between these extensions of the leak-barrier flaps 16 and the backsheet 20 so that the wings 18 can be easily gripped. The wings 18 are coated on respective rear surfaces with pressure-sensitive adhesive to form pressure-sensitive adhesive layers (not shown). To wear the napkin 10, the wings 18 may be folded back toward the rear surface side and the napkin 10 may be fastened to the wearer's shorts by means of the pressure-sensitive adhesive layer as illustrated by FIG. 2. In FIG. 2, leg-holes' peripheries of the wearer's shorts S are indicated by imaginary lines.

The napkin 10 is provided on its body-side surface 11 with a compressed groove 30 depressed toward the wearer's clothes-side surface 12. The compressed groove 30 defines a closed loop as a whole and generally comprises a pair of lateral groove segments 31, 31 extending in the longitudinal direction L in symmetry about the longitudinal center line C, a front side groove segment 32 extending from respective front ends 31a of these lateral groove segments 31, 31 so as to connect these lateral groove segments 31, 31 to each other, and a rear side groove segment 35 extending from respective rear ends 31b of these lateral groove segments 31, 31 so as to connect these lateral groove segments 31, 31 to each other.

The lateral groove segments 31, 31 are symmetric to each other about the longitudinal center line C and describe gentle curves which are slightly convex toward the longitudinal center line C.

The front side groove segment 32 comprises a front side inner groove segment 33 and a front side outer groove 34. Each of such inner and outer groove segments 33, 34 is bilaterally symmetric about the longitudinal center line C and describes gentle curve which is slightly convex toward the front end 13.

The rear side groove segment 35 comprises a rear side inner groove segment 36 and a rear side outer groove segment 39 lying rear- and outwardly of the rear side inner groove segment 36. Each of such inner and outer groove segments 36, 39 is bilaterally symmetric about the longitudinal center line C. Right and left halves of these inner and outer groove segments 36, 39 extend rearward from the rear ends 31b of the respective lateral groove segments 31, 31 so as to describe curves converging rearward. The rear side inner and outer groove segments 36, 39 respectively converge on the longitudinal center line C so as to define respective rear ends 36b, 39b lying on the longitudinal center line C. The rear side inner groove segment 36 has a shape pointed rearward more angularly than the front side inner groove segment 33 is pointed forward (See FIGS. 1 and 2). In the vicinity of the rear end 36b, the rear side inner groove segment 36 is curved so as to conform to an arc of a circle R indicated by imaginary line in FIG. 2 and inscribed in the vicinity of the rear end 36b. A radius of this imaginary inscribed circle R is preferably 10 mm or less.

The compressed groove 30 is obtained by at least partially compressing the topsheet 19 and the liquid-absorbent layer 21 under heating. The compressed groove 30 has a width preferably in a range of 1 to 5 mm, more preferably in a range of 2 to 3.5 mm. More specifically, the compressed groove 30 is obtained through a process of embossing with a heated roller. The compressed groove 30 comprises a high density compressed zones 50 in which the liquid-absorbent layer 21 and the topsheet 19 are pressure-bonded together and a medium density compressed zones 51 each interposed between each pair of the adjacent high density compressed zones 51 and having a density higher than in the region other than the compressed groove 30. Along the whole compressed groove as seen in FIG. 1, these high density compressed zone 50 and medium density compressed zone 51 alternately formed to define the linear groove depressed from the body-side surface 11 toward the wearer's clothes-side surface 12 of the napkin 10. In the vicinity of the longitudinal center line C, the front side inner and outer groove segments 33, 34 and the rear side inner and outer groove segments 36, 39 include the high density compressed zones 50 and the medium density compressed zones 51 extending in the longitudinal direction L.

When it is tried to apply the napkin to the region between the wearer's thighs, an intersection X at which the longitudinal center line C intersects an imaginary line segment extending in the transverse direction W to define the minimum distance between the pair of lateral groove segments 31, 31 or an intersection X' at which the longitudinal center line C intersects an imaginary line segment extending between middle points of the respective lateral groove segments 31, 31 may be used as a target for a position of the wearer's vaginal orifice. In the napkin 10 as illustrated, the intersection X substantially conforms with the intersection X'. In this napkin 10, a distance LX between the intersection X (X') and the front end 36a of the rear side inner groove segment 36 as measured in the longitudinal direction L is preferably in a range of 0 to 80 mm, more preferably in a range of 0 to 40 mm (See FIG. 2). As substitute for the intersection X or X', the middle of the most constricted zone of the napkin as viewed in the transverse direction W may be used as the target for the vaginal orifice.

A distance W36 between the proximal ends 36a of the respective rear side inner groove segment 36 is preferably in a range of 25 to 55 mm (See FIG. 2). A distance L36 from the proximal ends 36a to the rear end 36b of the rear side inner groove segment 36 as measured in the longitudinal direction L is preferably in a range of 30 to 150 mm.

An area surrounded by the compressed groove 30 is divided into a first absorbent zone 27 including the intersection X, a second absorbent zone 28 extending forward from the front side inner groove segment 33 and a third absorbent zone 29 extending rearward from the rear side inner groove segment 36. As will be understood from FIG. 5, the first absorbent zone 27 has a thickness H27 gradually reduced as viewed toward the rear end of this zone 27. The first absorbent zone 27 has the maximum thickness in the vicinity of the intersection X facing the wearer's vaginal orifice, which is preferably in a range of 1 to 15 mm, more preferably in a range of 5 to 12 mm and most preferably in a range of 6 to 10 mm. The second absorbent zone 28 has a thickness substantially same as a thickness of the third absorbent zone 29. The thickness H41 of the third absorbent zone 29 particularly in a bottom covering region 41 extending rearward from the rear end 36b of the rear side inner groove segment 36 is preferably in a range of 1 to 5 mm, more preferably in a range of 1.5 to 4 mm (See FIG. 4 also). However, it is not essential for implementation of the present invention that the thickness H27 of the first absorbent zone 27 is gradually reduced as viewed toward the rear end thereof but it is possible to form the first absorbent zone 27 to have a substantially uniform thickness H27. It is also possible without departing from the scope of the invention to form the second absorbent zone 27 to be thicker than the third absorbent zone 29.

The bottom covering region 41 presents a Gurley's flexural stiffness preferably in a range of 100 to 400 mg, more preferably in a range of 130 to 350 mg as measured in the transverse direction W.

Figure 6:
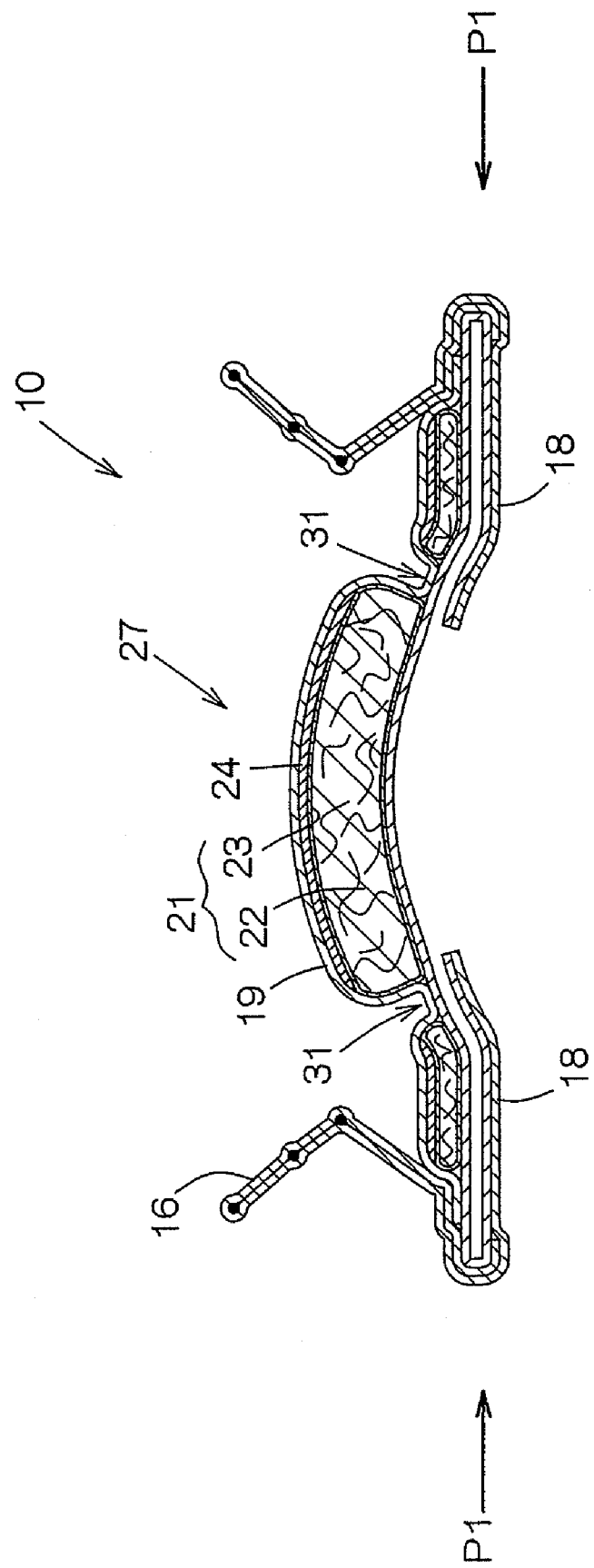
FIG. 6 is a view corresponding to FIG. 3, showing the sanitary napkin put on the wearer's body.
Figure 7:
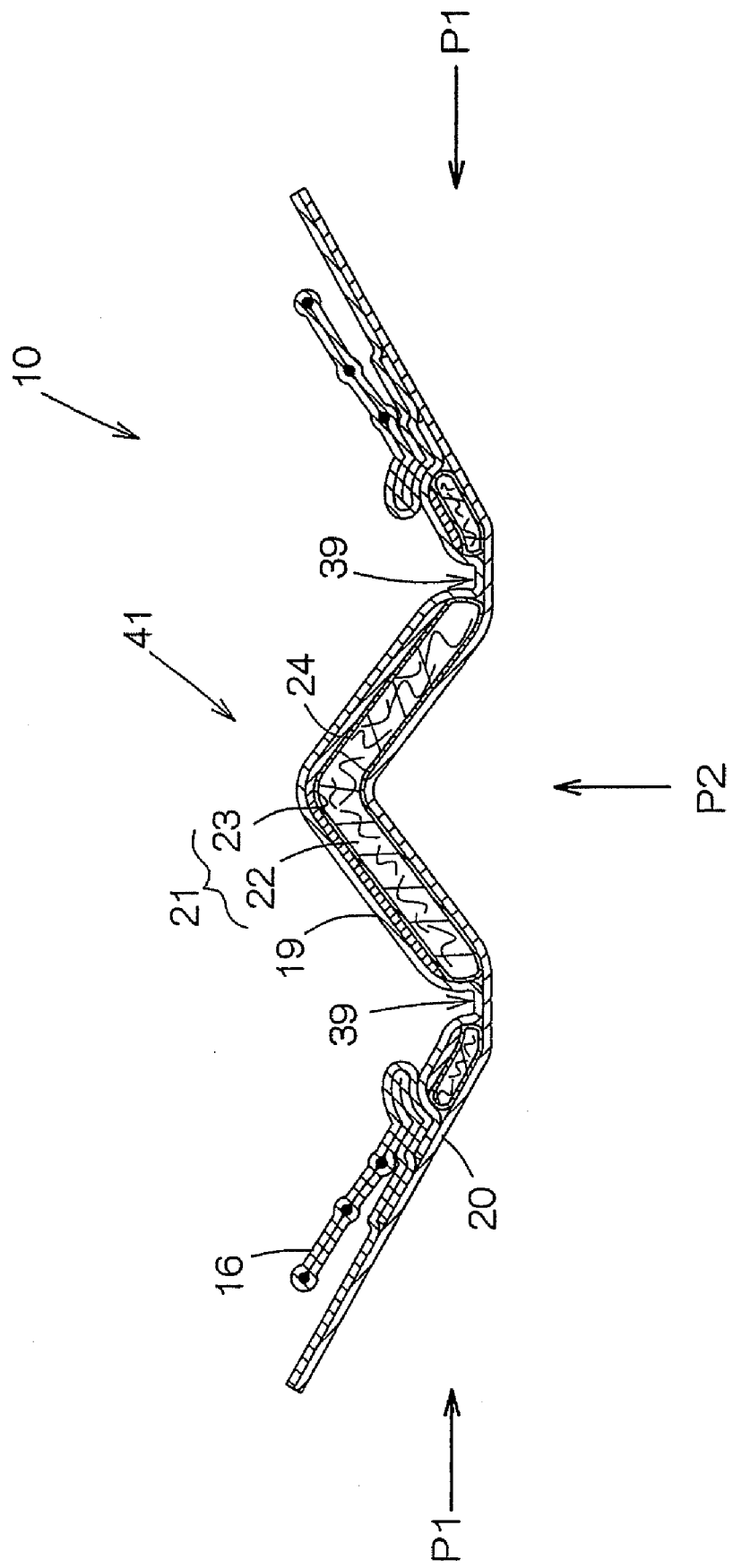
FIG. 7 is a view corresponding to FIG. 4, showing the sanitary napkin put on the wearer's body.

FIGS. 6 and 7 are views corresponding to FIGS. 3 and 4, respectively, showing the sanitary napkin 10 put on the wearer's body. The napkin 10 put on the wearer's body is subjected to a pressure P1 in the transverse direction W due to movement of the wearer's thighs and simultaneously subjected to a pressure P2 directed from the clothes-side surface 12 to the body-side surface 11 due to a contractile force of elastic yarns laid on the wearer's shorts so as to extend along the wearer's bottom cleft. Consequently, the zone 27 surrounded by the front side inner groove segment 34, the rear side inner groove segment 36 and the lateral groove segments 31 is deformed and thereby the body-side surface is lifted up. In the bottom covering region 41, at the same time, the pressure P1 is transmitted to the right and left halves 36, 38 of the rear side inner groove segment 36. Consequently, the bottom covering region 41 is folded along the rear side inner groove segment 36 to form a convexity with an apex defined by the longitudinal center line C.

The napkin 10 provided with the rear side inner groove segment 36 and the bottom covering region 41 as have been described above facilitates the bottom covering region 41 to be folded along the rear side inner groove segment 36 so as to form the convexity with the apex defined by the longitudinal center line C and thereby ensures the bottom covering region 41 folded in this manner to fit into the bottom cleft. In this manner, the bottom covering region 41 of the napkin 10 can reliably fit to the wearer's bottom and thereby prevent menstrual blood from flowing and leaking along the bottom cleft.

A distance L21 from the rear end 36b of the rear side inner groove segment 36 to the rear end 21b of the liquid-absorbent layer 21 as measured in the longitudinal direction L is preferably 50 mm or longer to assure an area of the bottom covering region 41 sufficient to cover a desired range of the wearer's bottom.

A distance L39 from the rear end 36b of the rear side inner groove segment 36 to the rear end 39b of the rear side outer groove segment 39 as measured in the longitudinal direction L is preferably 30 mm or longer, more preferably 40 mm or longer (See FIG. 2). By dimensioning the distance L39 in this manner, it is possible to generate, in this zone extending from the rear end 36b to the rear end 39b, a sufficiently long fold to ensure that the bottom covering region 41 can reliably fits to the wearer's bottom.

So far as the Gurley's flexural stiffness of the bottom covering region 41 as measured in the transverse direction W is in the above-mentioned range and the Gurley's flexural stiffness of the rear end 36b of the rear side inner groove segment 36 as measured in the transverse direction W is in a range of 100 to 400 mg, more preferably in a range of 130 to 350 mg, the bottom covering region 41 can be more smoothly folded along the rear side inner groove segment 36.

Figure 8:
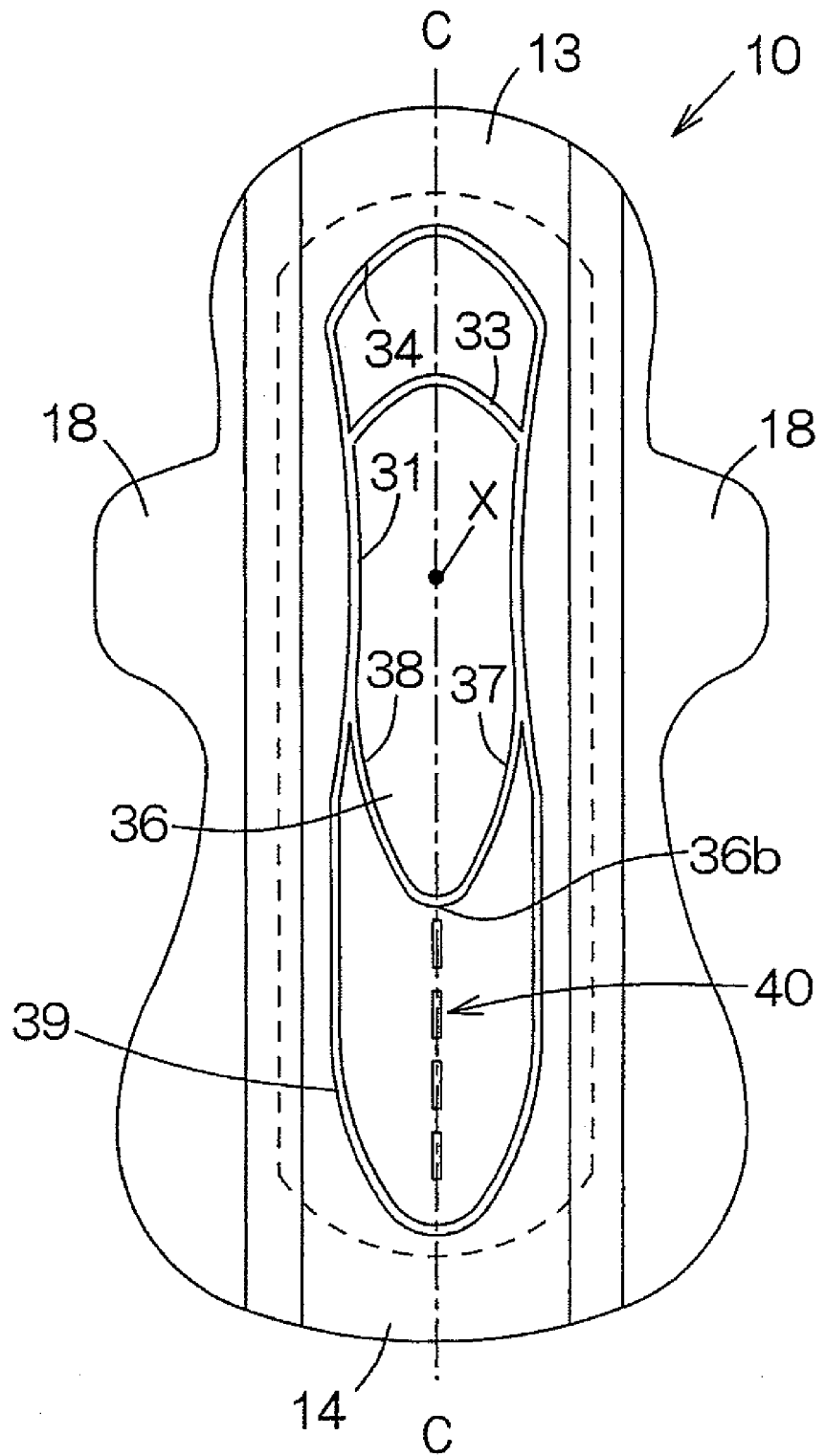
FIG. 8 is a plan view showing one preferred embodiment of the sanitary napkin.
Figure 9:
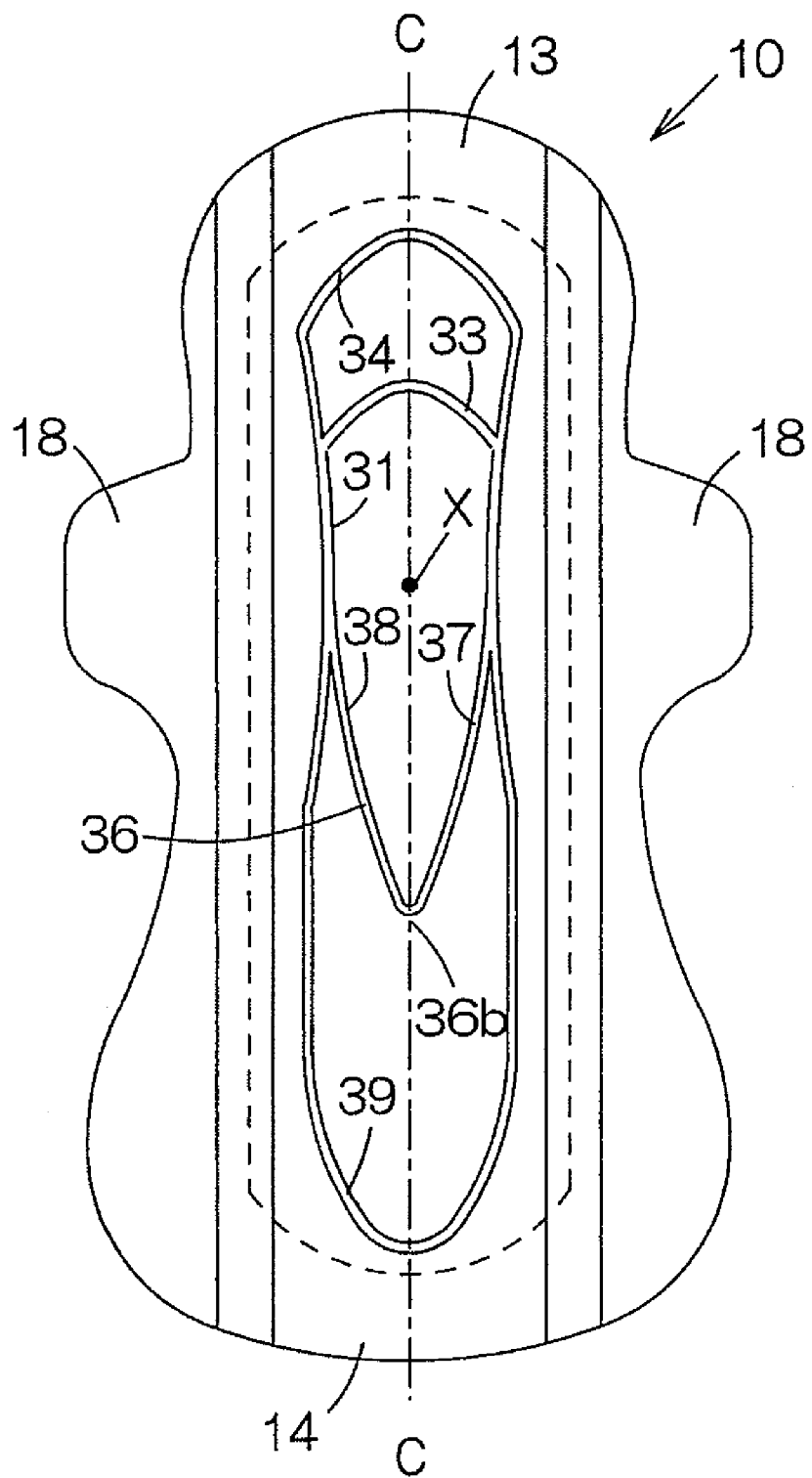
FIG. 9 is a plan view showing another preferred embodiment of the sanitary napkin.

Alternatively, it is possible to provide, as seen in FIG. 8, an auxiliary groove segment 40 serving as a guide for folding which extends rearward along the longitudinal center line C from the rear end 36b of the rear side inner groove segment 36 for the purpose of facilitating the bottom covering region 41 to be folded. This auxiliary groove 40 may be formed in the same manner as the compressed groove 30 or by providing the liquid-absorbent core 22 with slits.

Configuration of the rear side inner groove segment 36 is not limited to the configuration as shown by FIG. 1 and may be selected from those as shown by FIGS. 9 through 12.

Figure 12:
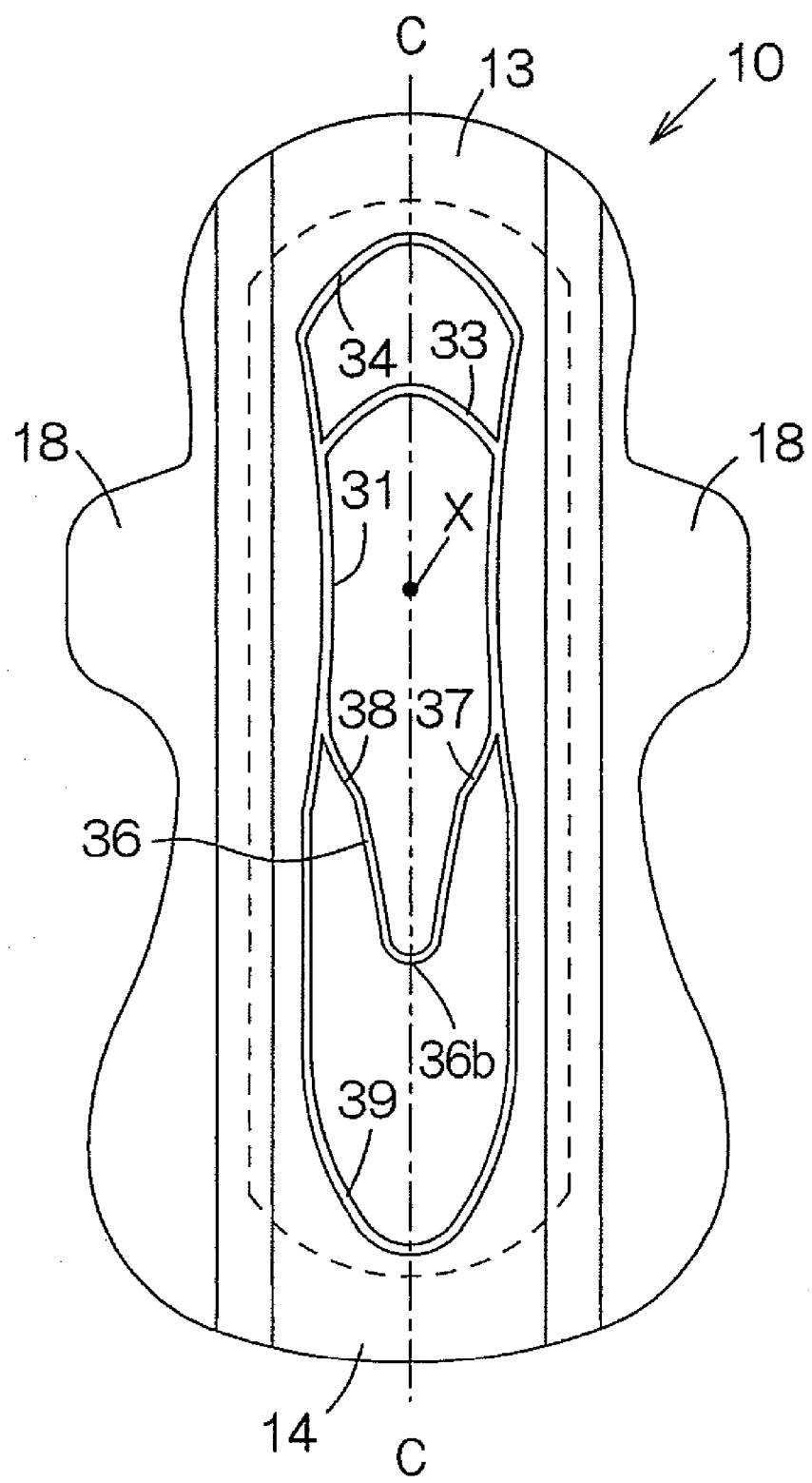
FIG. 12 is a plan view showing further another preferred embodiment of the sanitary napkin.

More specifically, the rear side inner groove segment 36 shown by FIG. 1 describes the parabolic gentle curve wherein the rear end 36b is rather rounded. In contrast with this, the rear side inner groove segment 36 shown by FIG. 9 has the rear end 36b which is rather angular. Of the rear side inner groove segment 36 shown by FIG. 10, right and left halves 37, 38 linearly extend and the rear end 36b is correspondingly pointed. The rear side inner groove segment 36 shown by FIG. 11 has right and left halves 37, 38 describing gentle curves slightly constricted toward the longitudinal center line C. Finally, the rear side inner groove segment 36 shown by FIG. 12 is stepwise tapered rearward.

Figure 10:
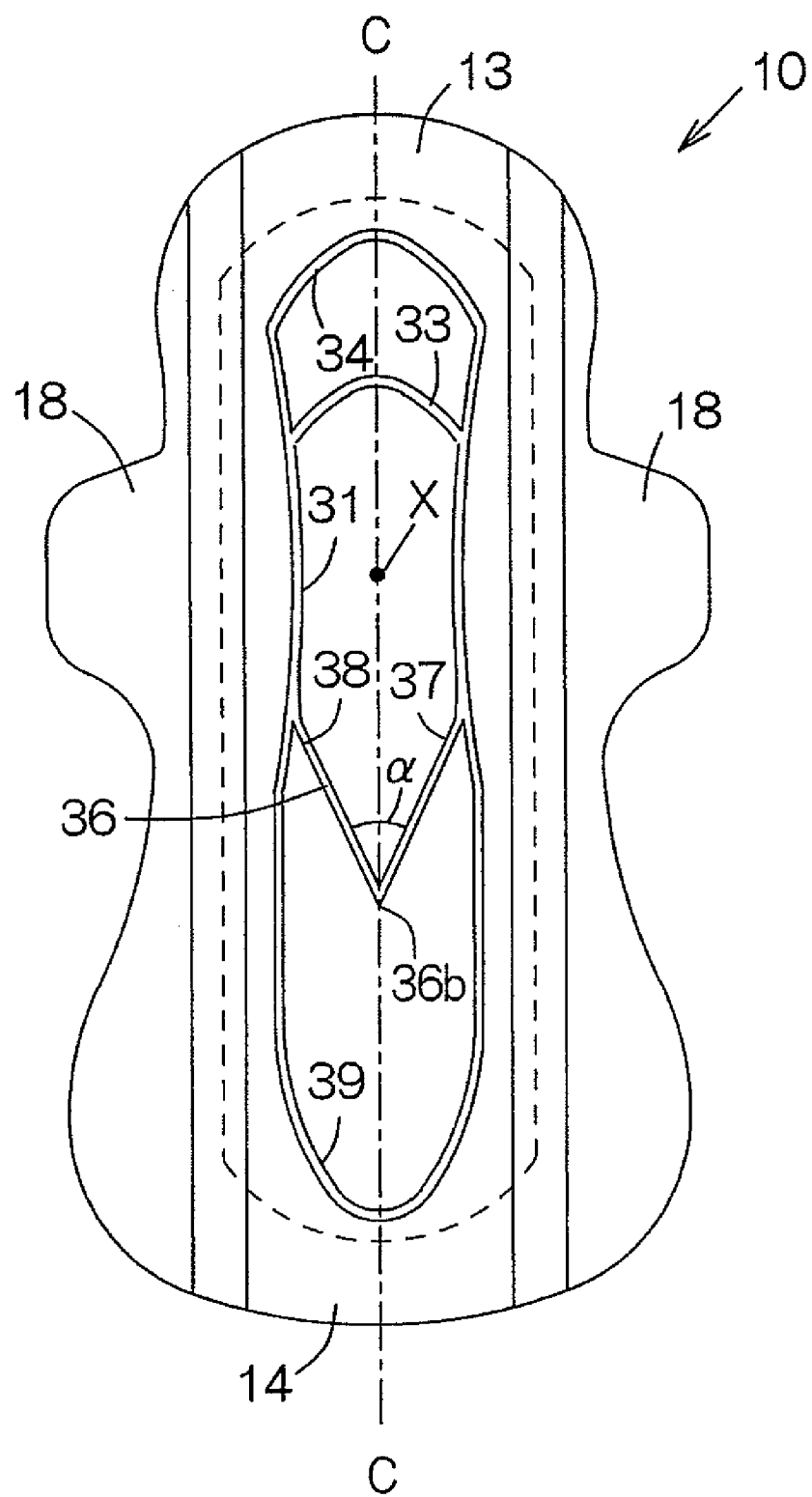
FIG. 10 is a plan view showing still another preferred embodiment of the sanitary napkin.
Figure 11:
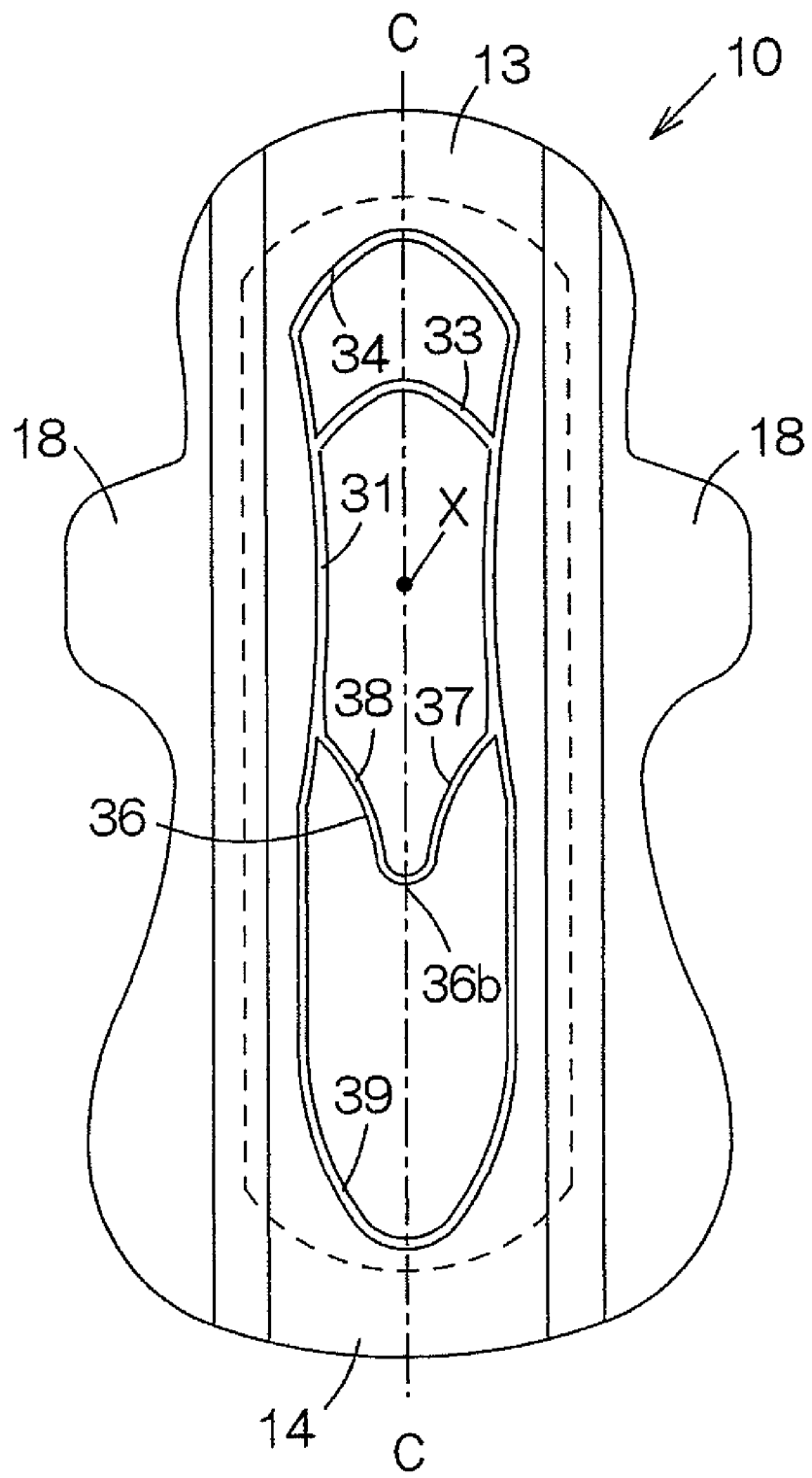
FIG. 11 is a plan view showing yet another preferred embodiment of the sanitary napkin.

The rear side inner groove segment 36 having the right and left halves 37, 38 linearly extending as shown in FIG. 10 corresponds to the case in which the radius of the circle R inscribed to the rear side inner groove segment 36 in the vicinity of the end 36b is 0 mm. An angle α included between these right and left halves 37, 38 is preferably in a range of 10 to 70°, more preferably in a range of 20 to 60°.

Figure 13:
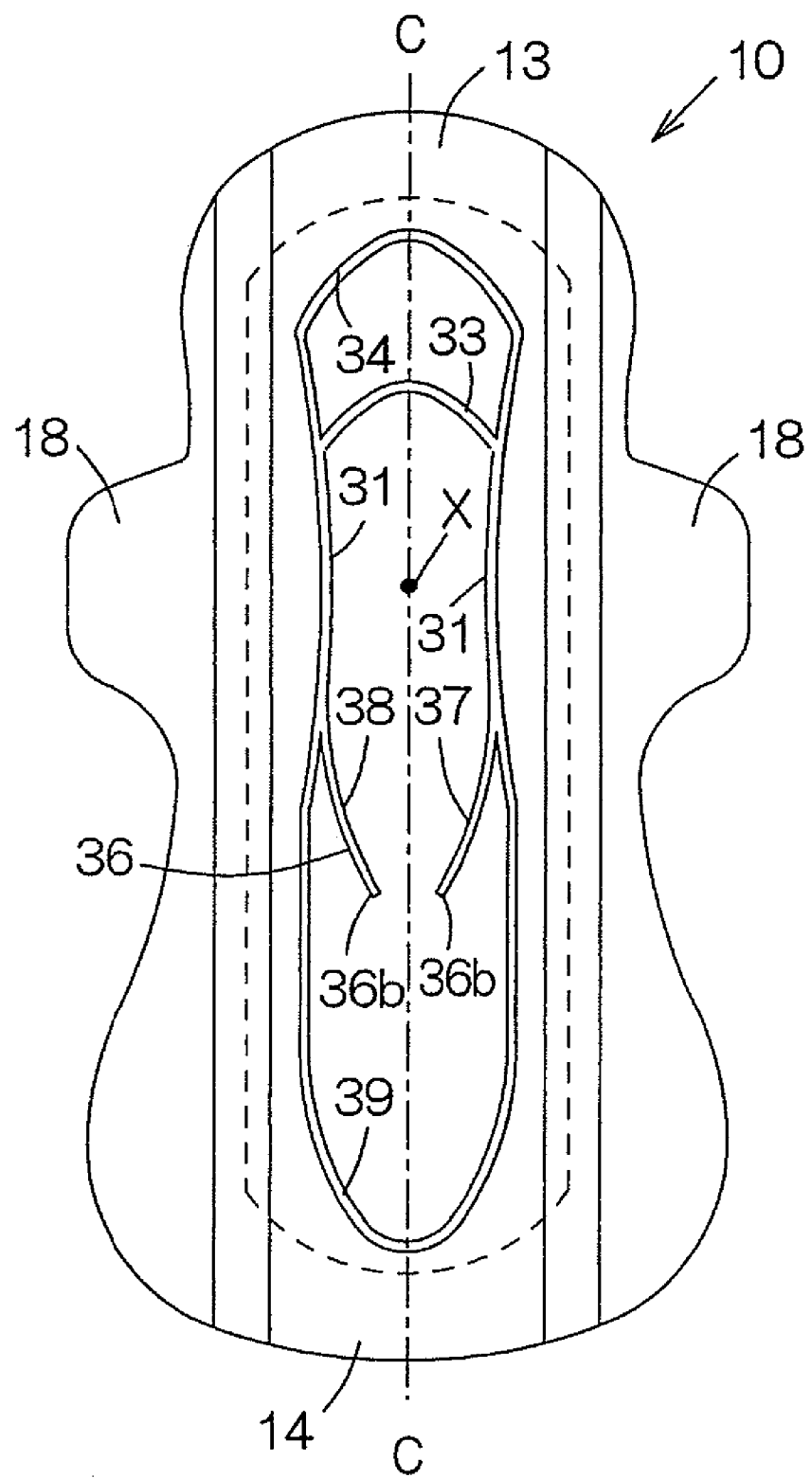
FIG. 13 is a plan view showing still another preferred embodiment of the sanitary napkin.

As shown by FIG. 13, the rear side inner groove segment 36 may be implemented in a manner that respective rear ends 36b of the right and left halves 37, 38 are not contiguous to each other. In this case, a middle point on an imaginary line segment connecting the rear ends 36b of the right and left halves 37, 38 preferably lies on the longitudinal center line C.

It is also possible to separate the proximal ends 36a of the rear side inner groove segment 36 from the rear ends 31a of the respective lateral groove segments 31 (not shown).

Figure 14:
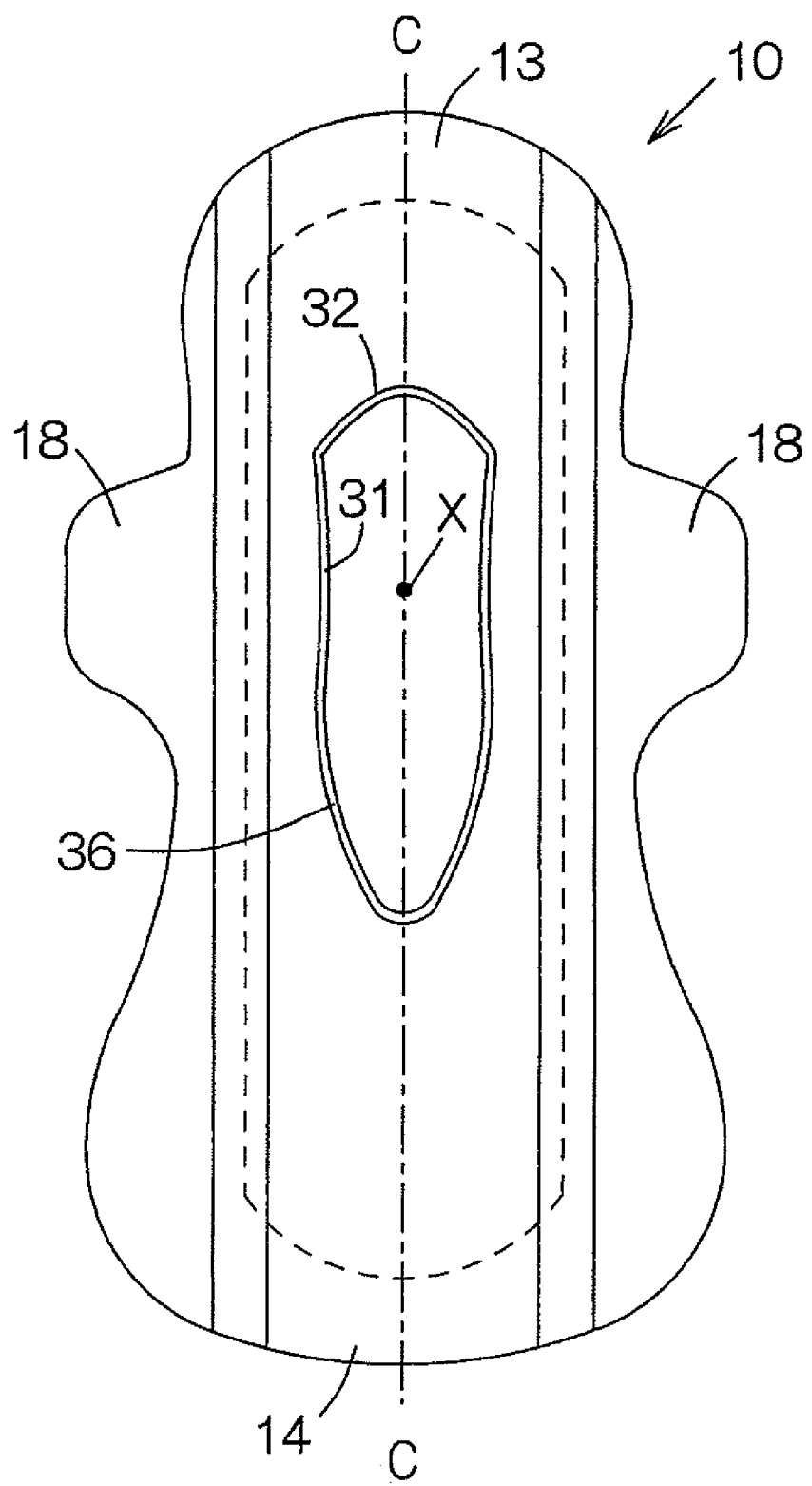
FIG. 14 is a plan view showing yet another preferred embodiment of the sanitary napkin.

Furthermore, the invention may be implemented in a manner that neither the front side groove segment 34 nor the rear side outer groove segment 39 is present, as shown by FIG. 14.

<Method for Measurement of Gurley's Flexural Stiffness>

Figure 15:
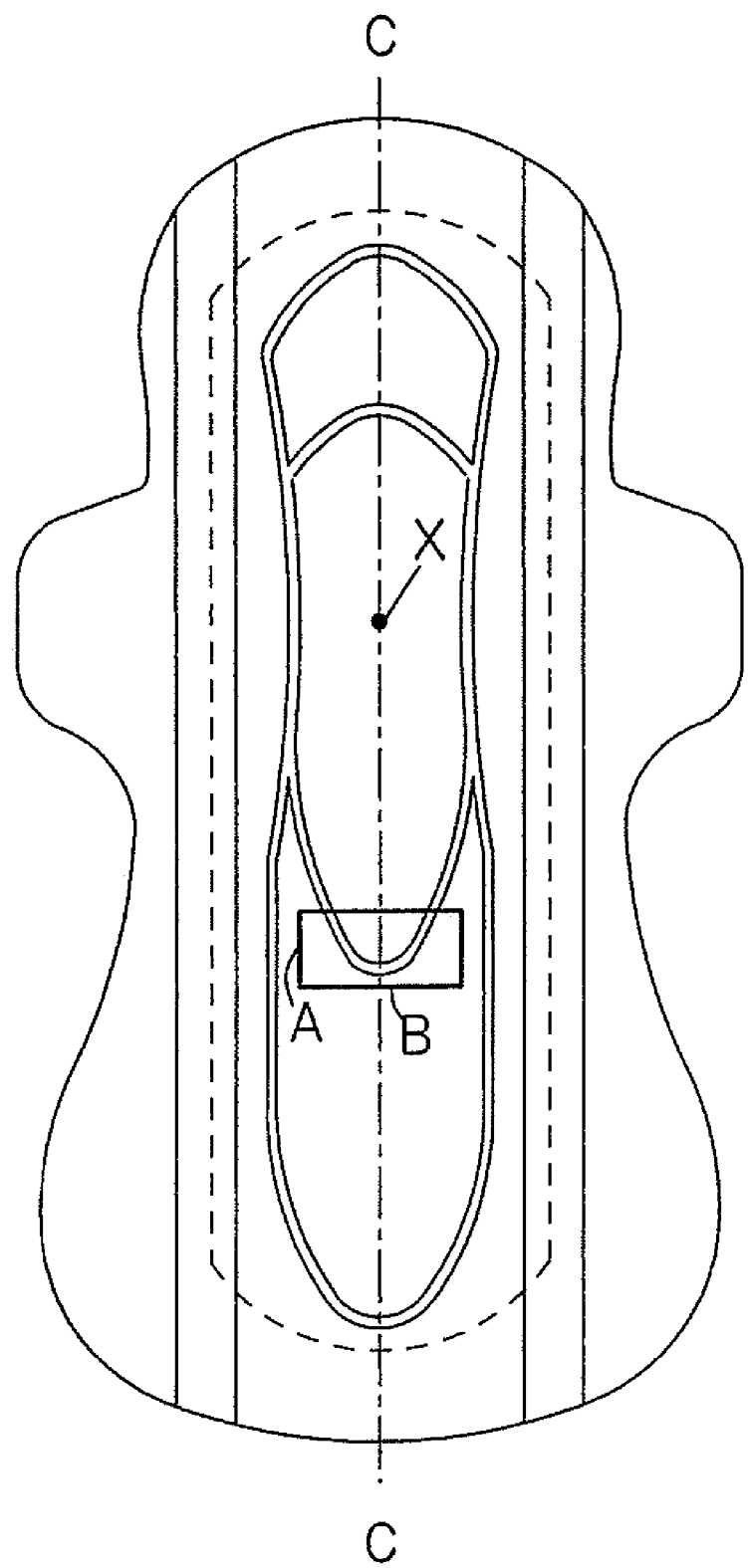
FIG. 15 is a plan view showing the sanitary napkin having been used to measure flexural stiffness.

To measure the Gurley's flexural stiffness, the region of the sanitary napkin 10 including the rear end 36b of the rear side inner groove segment 36 as enclosed by heavy line in FIG. 15 was cut off from the napkin 10 to prepare a specimen dimensioned to have a length A of 25 mm in the longitudinal direction L and a length B of 38 mm in the transverse direction W. For measurement, Gurley's Flexural Stiffness Tester (Model 311) manufactured by NISSHIN KIKAI Co., Ltd. was used.

More specifically, the specimen was held by a chuck along one of its transversely opposite lateral margins over a width of 3 mm from the edge of this margin while the other lateral margin was applied on the Tester's pendulum the transverse direction W. A flexural stiffness value was acquired with respect to the direction in which the body-side surface became convex measured and then a flexural stiffness value was acquired with respect to the direction in which the clothes-side surface became convex. An average of these two values of the flexural stiffness was calculated as a Gurley's flexural stiffness value.

Respective constitutive members of the napkin 10 may be selected from those commonly used in the related field of the art. For example, the topsheet 19 may be formed from air-through nonwoven fabric having a basis weight in a range of 15 to 70 g/m$^2$ and a density in a range of 0.01 to 0.025 g/cm$^3$ or perforated film having a basis weight in a range of 20 to 40 g/m$^2$. The backsheet 20 may be formed from liquid-impervious film of low density polyethylene (LDPE) having a basis weight in a range of 15 to 40 g/m$^2$. The liquid-absorbent core 22 may be formed by a mixture of fluff pulp having a basis weight in a range of 120 to 1000 g/m$^2$ and absorbent polymer having a basis weight in a range of 0 to 50 g/m$^2$. More specifically, the basis weight of fluff pulp is preferably in a range of 300 to 1000 g/m$^2$ so far as the first absorbent zone 27 is concerned and preferably in a range of 120 to 400 g/m$^2$ so far as the second and third absorbent zones 28, 29 are concerned. As the liquid-diffusive sheet 22, tissue having a basis weight in a range of 13 to 18 g/m$^2$ may be used. The cushion layer 24 may be formed by air-through nonwoven fabric having a basis weight in a range of 15 to 70 g/m$^2$ and a density in a range of 0.005 to 0.035 g/cm$^3$.

The present invention is applicable, not only to the sanitary napkin, but also to the other various types of absorbent articles such as vaginal discharge absorbent sheet and urine absorbent pad.

The entire discloses of Japanese Patent Application No. 2005-194361 filed on Jul. 1, 2005 including specification, drawings and abstract are herein incorporated by reference in its entirety.

What is claimed is:

1. An absorbent article having a longitudinal direction, a transverse direction, a body-side surface, a clothes-side surface, longitudinally opposed front and rear ends and transversely opposite side edges, said article comprising:
   a liquid-absorbent layer, and
   a continuous groove compressed into the body-side surface of the liquid-absorbent layer, wherein:
   said compressed groove comprises:

a pair of lateral groove segments extending substantially in said longitudinal direction and arranged symmetrically with respect to a longitudinal center line of said article, a front groove segment extending forward from respective front ends of said lateral groove segments so as to connect said front ends of said lateral groove segments together, said front groove segment defining a front side curve which is convex toward the front end of the article and which is symmetrical with respect to the longitudinal center line of said article, and a rear groove segment extending rearward from respective rear ends of said lateral groove segments so as to connect said rear ends of said lateral groove segments together, said rear groove segment defining a rear side curve which is convex toward the rear end of the article and which is symmetrical with respect to the longitudinal center line of said article, wherein said compressed groove as a whole presents an elongated, continuous and closed loop which is longer in the longitudinal direction than it is wide in the transverse direction;

said rear side curve has, in the vicinity of its rear end located on the longitudinal center line, a radius in a range of 0 to 10 mm;

said front side curve has, in the vicinity of its front end located on the longitudinal center line, a radius greater than the radius of the rear side curve; and said absorbent layer comprises a bottom covering region which extends rearward from the rear end of said rear groove segment, has a thickness in a range of 1 to 5 mm, and is adapted to be folded along the longitudinal center line so that said bottom covering region can become convex, in use, toward a wearer;

wherein a thickness of the absorbent layer within the closed-loop shape defined by the compressed groove decreases gradually in the longitudinal direction from a front portion in the vicinity of the front end of the front groove segment to a rear portion in the vicinity of the rear end of the rear groove segment.

2. The article defined by claim 1, wherein said bottom covering region has a flexural stiffness in a range of 100 to 400 mg as measured in said transverse direction.

3. The article defined by claim 1, wherein the distance from the rear end of said rear groove segment to the rear end of said liquid-absorbent layer as measured in said longitudinal direction is 50 mm or longer.

4. The article as defined by claim 1, wherein the lateral groove segments are convex inwardly toward the longitudinal center line.

5. The article as defined by claim 1, wherein said continuous, compressed groove further comprises:

an outer front groove segment located forward of the front groove segment and extending forward from the respective front ends of said lateral groove segments so as to connect said front ends of said lateral groove segments together, said outer front groove segment defining an outer front side curve which is convex toward the front end of the article and which is symmetrical with respect to the longitudinal center line of said article, and an outer rear groove segment located rearward of the rear groove segment and extending rearward from the respective rear ends of said lateral groove segments so as to connect said rear ends of said lateral groove segments together, said outer rear groove segment defining an outer rear side curve which is convex toward the rear end of the article and which is symmetrical with respect to the longitudinal center line of said article, wherein said outer front and rear groove segments and said lateral groove segments together define an elongated, continuous and closed outer loop which is longer the in longitudinal direction that it is wide in the transverse direction; and said front and rear groove segments and said lateral groove segments together define said elongated, continuous and closed loop which is an inner loop.

6. The article as defined by claim 5, wherein the longitudinal center line intersects an imaginary line, which extends in the transverse direction and defines the minimum distance between the lateral groove segments, at an intersection that is adapted to be a target for a position of a wearer's vaginal orifice in use; and each of said inner and outer loops is asymmetrical with respect to said imaginary line, with the front side curve or the outer front side curve being closer, in the longitudinal direction, to the imaginary line than the rear side curve or the outer rear side curve, respectively;

a distance, as measured in said transverse direction, between said rear ends of said lateral groove segments, from which the rear side curve and the outer rear side curve branch, is in a range of 25 to 55 mm;

a distance, as measured in said longitudinal direction, from said rear ends of said lateral groove segments to the rear end of the rear groove segment is in a range of 30 to 150 mm; and a distance, as measured in said longitudinal direction, from the rear end of the rear groove segment to the rear end of the outer rear groove segment is 40 mm or longer.

7. The article defined by claim 6, wherein a distance, as measured in said longitudinal direction, from the rear end of the rear groove segment to the rear end of the absorbent layer is 50 mm or longer.

8. The article defined by claim 7, wherein the distance from the rear ends of said lateral groove segments to the imaginary line as measured in said longitudinal direction is in a range of 0 to 80 mm.

9. The article defined by claim 1, wherein a bottom of the compressed groove is free of absorbent material.

10. An absorbent article having a longitudinal direction, a transverse direction, a body-side surface, a clothes-side surface, longitudinally opposed front and rear ends and transversely opposite side edges, said article comprising:

a liquid-absorbent layer, and a continuous groove compressed into the body-side surface of the liquid-absorbent layer, wherein:

said compressed groove comprises:

a pair of lateral groove segments extending substantially in said longitudinal direction and arranged symmetrically with respect to a longitudinal center line of said article, a front groove segment extending forward from respective front ends of said lateral groove segments so as to connect said front ends of said lateral groove segments together, said front groove segment defining a front side curve which is convex toward the front end of the article and which is symmetrical with respect to the longitudinal center line of said article, and a rear groove segment extending rearward from respective rear ends of said lateral groove segments so as to connect said rear ends of said lateral groove segments together, said rear groove segment defining a rear side curve which is convex toward the rear end of the article and which is symmetrical with respect to the longitudinal center line of said article, wherein said compressed groove as a whole presents an elongated, continuous and closed loop which is longer in the longitudinal direction than it is wide in the transverse direction;

the longitudinal center line intersects an imaginary line, which extends in the transverse direction and defines the minimum distance between the lateral groove segments, at an intersection that is adapted to be a target for a position of a wearer's vaginal orifice in use; and said compressed groove is asymmetrical with respect to said imaginary line, with the front side curve being closer, in the longitudinal direction, to the imaginary line than the rear side curve;

a distance between said rear ends of said lateral groove segments as measured in said transverse direction is in a range of 25 to 55 mm;

a distance from said rear ends of said lateral groove segments to the rear end of the rear groove segment as measured in said longitudinal direction is in a range of 30 to 150 mm; and said absorbent layer comprises a bottom covering region which extends rearward from the rear end of said rear groove segment, has a thickness in a range of 1 to 5 mm, and is adapted to be folded along the longitudinal center line so that said bottom covering region can become convex, in use, toward a wearer;

wherein a thickness of a majority of the absorbent layer within the closed-loop shape defined by the compressed groove decreases gradually in the longitudinal direction from the front groove segment to the rear groove segment.

11. The article as defined by claim 10, wherein said rear side curve has, in the vicinity of its rear end located on the longitudinal center line, a radius in a range of 0 to 10 mm; and said front side curve has, in the vicinity of its front end located on the longitudinal center line, a radius greater than the radius of the rear side curve.

12. The article defined by claim 11, wherein the distance from the rear end of said rear groove segment to the rear end of said liquid-absorbent layer as measured in said longitudinal direction is 50 mm or longer.

13. The article defined by claim 10, wherein the distance from the rear ends of said lateral groove segments to the imaginary line as measured in said longitudinal direction is in a range of 0 to 80 mm.

14. The article defined by claim 10, wherein a bottom of the compressed groove is free of absorbent material.

15. An absorbent article having a longitudinal direction, a transverse direction, a body-side surface, a clothes-side surface, longitudinally opposed front and rear ends and transversely opposite side edges, said article comprising:

a liquid-absorbent layer, and a continuous groove compressed into the body-side surface of the liquid-absorbent layer, wherein:

said compressed groove comprises:

a pair of lateral groove segments extending substantially in said longitudinal direction and arranged symmetrically with respect to a longitudinal center line of said article, a front groove segment extending forward from respective front ends of said lateral groove segments so as to connect said front ends of said lateral groove segments together, said front groove segment defining a front side curve which is convex toward the front end of the article and which is symmetrical with respect to the longitudinal center line of said article, and a rear groove segment extending rearward from respective rear ends of said lateral groove segments so as to connect said rear ends of said lateral groove segments together, said rear groove segment defining a rear side curve which is convex toward the rear end of the article and which is symmetrical with respect to the longitudinal center line of said article, wherein said compressed groove as a whole presents an elongated, continuous and closed loop which is longer in the longitudinal direction than it is wide in the transverse direction;

a thickness of the absorbent layer within the closed-loop shape defined by the compressed groove decreases gradually in the longitudinal direction from the front groove segment to the rear groove segment; and wherein the lateral groove segments are convex inwardly toward the longitudinal center line.

16. The article defined by claim 15, wherein a bottom of the compressed groove is free of absorbent material.

17. The article defined by claim 15, wherein the thickness of the absorbent layer within the closed-loop shape and on the longitudinal center line is highest at a first point located in the vicinity of and forward of said front ends of the lateral groove segments, and the thickness of the absorbent layer decreases gradually along the longitudinal center line to a second point located in the vicinity of and rearward of said rear ends of the lateral groove segments.

18. The article defined by claim 17, wherein a bottom of the compressed groove is free of absorbent material.

* * * * *